United States Patent [19]

Hoffman

[11] 4,001,336

[45] Jan. 4, 1977

[54] 2,6,10-TRIMETHYL-DODECAN-1-AL AND 2,6,10-TRIMETHYL-DODECA-4,8-DIEN-1-AL

[75] Inventor: Werner Hoffman, Neuhofen, Germany

[73] Assignee: BASF Aktiengesellschaft, Ludwigshafen (Rhine), Germany

[22] Filed: Aug. 1, 1975

[21] Appl. No.: 601,023

[30] Foreign Application Priority Data

Aug. 16, 1974 Germany .......................... 2439198

[52] U.S. Cl. ........................... 260/601 R; 252/522; 426/534
[51] Int. Cl.$^2$ ......................................... C07C 47/02
[58] Field of Search ................................ 260/601 R

[56] References Cited

UNITED STATES PATENTS 2,815,386   12/1957   Surmatis ....................... 260/601 R

OTHER PUBLICATIONS

Chang, "Chemical Abstracts" vol. 59 (1963) 3869–3874 especially 3871e.
Schudel et al. "Chemical Abstracts" vol. 59 (1963) 2757–2758, esp. 2758.

Primary Examiner—James O. Thomas, Jr.
Assistant Examiner—W. B. Lone
Attorney, Agent, or Firm—Johnston, Keil, Thompson & Shurtleff

[57] ABSTRACT

2,6,10-Trimethyl-dodecan-1-al and its 4,8-diene and processes for their manufacture. The new compounds are manufactured by vinylation or ethynylation and subsequent partial hydrogenation of 2-methyl-butan-1-al, reaction of the resulting 4-methyl-hex-1-en-3-ol with a propenyl ether in the presence of an acid catalyst at elevated temperatures, or reaction of the resulting 4-methyl-hex-1-en-3-ol with an α-formyl-propionic acid ester at elevated temperatures, subsequent vinylation of ethynylation and partial hydrogenation of the resulting 2,6-dimethyl-oct-4-en-1-al, renewed reaction with a propenyl ether or an α-formyl-propionic acid ester and — if desired — catalytic hydrogenation of the resulting 2,6,10-trimethyl-dodeca-4,8-dien-1-al. The organoleptic properties of the new compounds greatly resemble those of the natural scents and aromas of oranges, namely α- and β-sinensal. They have the advantage over the sinensals of being more stable to acid and alkali, and are therefore particularly suitable for flavoring, eg., carbonated beverages, or for perfuming alkaline products. In addition they are industrially substantially simpler to produce than are the sinensals.

2 Claims, No Drawings

2,6,10-TRIMETHYL-DODECAN-1-AL AND 2,6,10-TRIMETHYL-DODECA-4,8-DIEN-1-AL

The present invention relates to 2,6,10-trimethyl-dodecan-1-al and its 4,8-diene, ie. to compounds of the general formula I

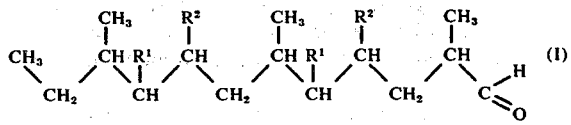

where $R^1$ and $R^2$ are each hydrogen or together are a second bond between the carbon atoms on which they are present, and to a multi-stage process for their manufacture.

The organoleptic properties of both the new compounds are, surprisingly, very similar to those of the natural orange aromas α- and β-sinensal. However, the new compounds are substantially more stable to acid and alkali than the sinensals, and are therefore very particularly suitable for flavoring, eg., carbonated beverages, or for perfuming alkaline products. In addition, the new compounds are industrially substantially simpler, and therefore cheaper, to produce than α-sinensal and β-sinensal themselves.

We have found a process for the manufacture of the compounds according to the invention, of the formula I, wherein a. 2-methyl-butan-1-al is converted into 4-methyl-hex-1-en-3-ol by reaction with a solution of a vinyl-magnesium halide or by ethynylation and subsequent partial hydrogenation, b. the resulting 4-methyl-hex-1-en-3-ol is reacted, in the presence of an acid catalyst, at elevated temperatures, with a propenyl ether of the formula II

in which R' is alkyl of 1 to 4 carbon atoms, or with an α-formyl-propionic acid ester of the formula III

in which R'' is alkyl of 1 to 4 carbon atoms, at elevated temperatures, c. the resulting 2,6-dimethyl-oct-4-en-1-al is vinylated as described under (a), or ethynylated and subsequently partially hydrogenated, d. the resulting 4,8-dimethyl-deca-1,6-dien-3-ol is reacted, as described under (b), with a propenyl ether of the formula II or an α-formyl-propionic acid ester of the formula III and e. if $R^1$ and $R^2$ in I are each hydrogen, the resulting 2,6,10-trimethyl-dodeca-4,8-dien-1-al is catalytically hydrogenated by conventional methods.

2-Methyl-butan-1-al required as the starting compound may be obtained industrially by simple methods, eg. hydroformylation of 2-butene.

The reaction of 2-methyl-butan-1-al or 2,6-dimethyl-oct-4-en-1-al with the solution of vinyl-magnesium halide is in general carried out by the conventional method used for Grignard reactions, at from about −20° to +60° C, preferably from 0° to 40° C.

Vinyl-magnesium halides which may be used are vinyl-magnesium chloride, vinyl-magnesium bromide and vinyl-magnesium iodide, especially vinyl-magnesium chloride. The vinyl-magnesium halide solutions are produced by conventional methods, ie. reaction of vinyl chloride, vinyl chloride, vinyl bromide or vinyl iodide with magnesium in ether-type solvents, eg. diethyl ether, tetrahydrofuran or diethylene glycol dimethyl ether. The strength of the solutions used is from 0.5 to 5 molar, preferably from about 1 to 2 molar. To achieve as nearly complete conversion of the ketone as possible, it is advisable to use about a 10% molar excess of the vinyl-Grignard compound.

To hydrolyze the magnesium alcoholates formed it is advisable to use only the amount of water required to form the salt, ie. about 100 ml of water per mole of magnesium. The reaction products may be isolated in the conventional way by filtration and fractional distillation of the organic phase obtained. 2-Methyl-butan-1-al or 2,6-dimethyl-oct-4-en-1-al may also be converted respectively into 4-methyl-hex-1-en-3-ol and 4,8-dimethyl-deca-1,6-dien-3-ol by ethynylation and subsequent partial hydrogenation.

The ethynylation is carried out either by reaction with a solution of ethynyl-magnesium halides under the conditions described for the reaction of vinyl-magnesium halides or by reaction of the aldehydes with acetylene in inert organic solvents in the presence of heavy metal acetylides, such as copper acetylide or silver acetylide, or in the presence of basic catalysts, such as sodium acetylide or potassium acetylide, or the oxides, hydroxides, alcoholates or amides of the alkali metals or alkaline earth metals, or in the presence of anion exchangers containing quaternary ammonium groups (cf., eg., Belgian Pat. No. 725,275). It is particularly advantageous to carry out the reaction with acetylene in the presence of acetylides of sodium, potassium, lithium or magnesium or of compounds which are able to form these acetylides under the reaction conditions, such as oxides or hydroxides, alcoholates or amides of these metals, and in solvents such as diethyl ether, tetrahydrofuran, N-methylpyrrolidone or dimethylformamide. The ethynylation is carried out at from −20° to +60° C, preferably from 0° to +40° C, and at pressures from atmospheric pressure to about 30 atmospheres. The reaction products are worked up and isolated by hydrolysis and fractional distillation of the organic phase, as described above.

The partial hydrogenation of the resulting acetylene alcohols to give 4-methyl-hex-1-en-3-ol or 4,8-dimethyl-deca-1,6-dien-3-ol may be carried out in the presence or absence of solvents, but is particularly advantageously carried out in their presence. Solvents such as alcohols, eg. methanol and ethanol, ethers, eg. tetrahydrofuran, diethyl ether, dioxane and trioxane, and esters, such as ethyl acetate and methyl propionate, are particularly suitable for the purpose.

Supported palladium catalysts which contain from 0.01 to 5 per cent by weight of palladium are particularly suitable catalysts for the reaction. Specific examples of catalyst carriers are calcium carbonate, aluminum oxide and silicon dioxide. The selectivity may be increased by deactivating the said catalysts, eg. in accordance with German Pat. No. 1,115,238 by treatment with zinc ions or lead ions.

The partial hydrogenation is in general carried out under atmospheric pressure or at hydrogen pressures of from 0.1 to 1 atmosphere, and at from about 0° to 80° C, preferably from 15° to 35° C.

The reaction of 4-methyl-hex-1-en-3-ol and of 4,8-dimethyl-deca-1,6-dien-3-ol with a propenyl ether of the formula II is in general carried out in the manner described in German Pat. No. 1,193,490 which is incorporated herein by reference. Phosphoric acid is therefore a particularly suitable acid catalyst for this reaction. The concentration of phosphoric acid in the reaction mixture is suitably from about 0.01 to 0.5 per cent by weight and especially 0.2 per cent by weight. However, other mineral acids, in similar concentration, eg. sulfuric acid, may be used as catalysts, as may strong organic acids, eg. oxalic acid, trichloroacetic acid or p-toluenesulfonic acid. Acid salts, eg. potassium bisulfate, or Lewis acids, eg. boron trichloride, boron trifluoride and zinc chloride may also be used as acid catalysts.

The reaction according to the invention is carried out at elevated temperatures, eg. above about 50° C, and suitably at above about 100° C, ie. at from about 100° to 250° C. Temperatures of from about 120° to 200° C are generally preferred.

The reaction may be carried out with or without solvents. Examples of solvents which may be used are hydrocarbons, eg. hexane, cyclohexane, isooctane, benzene, toluene, petroleum ether and ligroin.

In general it is advantageous to carry out the reaction of the starting materials under superatmospheric pressure. To achieve this it is possible, eg., to heat the starting materials in a closed vessel. The pressure can be further increased by injecting an inert gas, eg. nitrogen. However, the reaction may also be carried out under atmospheric pressure, eg. by heating the starting materials under reflux, suitably in the presence of one of the above solvents.

The reaction times naturally vary greatly with the reaction temperatures. To achieve optimum yields, the progress of the reaction is suitably followed by analysis of samples, eg. by gas chromatography, and heating is discontinued as soon as the allyl alcohol component has been completely converted.

2,6-Dimethyl-oct-4-en-1-al and 2,6,10-trimethyl-dodeca-4,8-dien-1-al may be isolated from the mixture of the reaction products by conventional methods, eg. by fractional distillation. Prior to the distillation, the acid catalyst is preferably neutralized, by adding an inorganic or organic base, eg. sodium acetate, sodium hydroxide, sodium carbonate, ammonia, or a tertiary amine, such as triethylamine or pyridine, and is then removed from the reaction mixture, if appropriate.

The reaction may also readily be carried out continuously, eg. by passing the reaction mixture under pressure through a tube heated to elevated temperatures and maintaining residence times which ensure substantially complete conversion of the starting materials.

The reaction of 4-methyl-hex-1-en-3-ol and 4,8-dimethyl-deca-1,6-dien-3-ol with α-formyl-propionic acid esters is in general carried out at from 100° to 350° C, and particularly good results are obtained at from 120° to 220° C. In general, the reaction is carried out under atmospheric pressure, but pressures of from 100 mm Hg to 10 atmospheres may also be used.

In general, the reaction is carried out without using solvents or diluents. However, it is also possible to use inert high-boiling hydrocarbons, such as perhydronaphthalene, or tetrahydronaphthalene, dimethylformamide or N-methyl-pyrrolidone, as solvents or diluents.

It is advantageous to use from 1 to 5 moles, preferably from 1.2 to 2.5 moles, of the α-formyl-propionic acid ester per mole of starting material. To carry out this stage of the process, a mixture of the starting alcohol and of the α-formyl-propionic acid ester in the stated ratio is in general introduced into a reaction vessel and heated to the reaction temperature; the end of the reaction is readily ascertainable from the cessation of elimination of carbon dioxide. The reaction mixture is then worked up — where appropriate, after distilling off any solvent used — by using conventional methods, eg., fractional distillation. Unconverted starting materials may be recycled to the reaction. The reaction is also simple to carry out continuously.

The catalytic hydrogenation of 2,6,10-trimethyl-dodeca-4,8-dien-1-al is carried out by conventional methods and with conventional hydrogenation catalysts, examples of which are platinum, nickel, cobalt, ruthenium and rhodium catalysts.

Supported palladium catalysts, such as $Pd/SiO_2$, $Pd/Al_2O_3$, Pd/charcoal and the like, are particularly suitable. The reaction is preferably carried out in a solvent which is inert under the reaction conditions, eg. methanol, ethyl acetate or tetrahydrofuran, at from 20° to 120° C and with hydrogen pressures of from 0 to 250 atmospheres gauge. In general, the 2,6,10-trimethyl-dodecan-1-al is purified by simple distillation.

Using the multi-stage process of the invention it is possible to manufacture the new compounds 2,6,10-trimethyl-dodecan-1-al and 2,6,10-trimethyl-dodeca-4,8-dien-1-al in a technically elegant manner. The organoleptic properties of the new compounds greatly resemble those of the natural scents and aromas of oranges, namely α- and β-sinensal. They have the advantage over the sinensals of being more stable to acid and alkali, and are therefore particularly suitable for flavoring, eg., carbonated beverages, or for perfuming alkaline products. In addition they are industrially substantially simpler to produce than are the sinensals.

The Examples which follow show a useful embodiment of the above process.

EXAMPLE 1

(a) 4-Methyl-hex-1-en-3-ol 215 g (2.5 moles) of 2-methylbutan-1-al are added to a solution of 2.6 moles of vinyl-magnesium chloride in 2 liters of tetrahydrofuran in the course of one hour, whilst cooling with ice. After a reaction time of one hour, the mixture is hydrolyzed with 260 ml of water and the organic phase is isolated. The solvent is distilled off and the reaction product is fractionated, giving 263 g of the allyl alcohol 4-methyl-hex-1-en-3-ol. This corresponds to a yield of 93% of theory, based on 2-methylbutan-1-al employed. B.p. = 75° – 77° C at 50 mm Hg; $n_D^{25}$ = 1.4346.

(b) 2,6-Dimethyl-oct-4-en-1-al 57 g (0.5 mole) of 4-methyl-hex-1-en-3-ol and 70 g of α-formylpropionic acid methyl ester (0.6 mole) are heated at from 140° to 200° C whilst stirring; at the same time the methanol liberated is distilled off through a 20 cm column and the carbon dioxide is measured using a gas flow meter. 11.5 liters of carbon dioxide are liberated in the course of three hours. When the elimination of methanol and carbon dioxide has ceased, the mixture is fractionated. 58 g of the above aldehyde (yield: 75% of theory) are obtained. B.p. = 75° – 80° C at 11 mm Hg.

(c) 4,8-Dimethyl-decan-1,6-dien-3-ol 54 g (0.35 mole) of 2,6-dimethyl-oct-4-en-1-al are added in the course of 15 minutes to a solution of 0.4 mole of vinyl-magnesium chloride in 2 liters of tetrahydrofuran, whilst cooling with ice. After a reaction time of 30 minutes, the mixture is hydrolyzed with 40 ml of water, the organic phase is isolated and the solvent is distilled off. The reaction product is fractionated, giving 60 g of the above allyl alcohol (yield, 94% of theory). B.p. = 48°–52° C at 0.02 mm Hg; $n_D^{25}$ = 1.4591.

(d) 2,6,10-Trimethyl-dodeca-4,8-dien-1-al 55 g (0.3 mole) of 4,8-dimethyl-deca-1,6-dien-3-ol and 46 g (0.4 mole) of α-formyl-propionic acid methyl ester are heated at from 140° to 200° C, whilst stirring, the methanol thereby eliminated is distilled off through a column, and the carbon dioxide eliminated is recorded by a gas flow meter. When the reaction has ceased, the contents of the flask are fractionated. 51 g of 2,6,10-trimethyl-dodeca-4,8-dien-1-al (yield, 77% of theory) are obtained. B.p. = 72° – 75° C at 0.01 mm Hg; $n_D^{25}$ = 1.4566. Odor: sweet, fruity, orange scent.

EXAMPLE 2

2,6,10-Trimethyl-dodecan-1-al 22 g (0.1 mole) of 2,6,10-trimethyl-dodeca-4,8-dien-1-al are dissolved in 20 ml of tetrahydrofuran, 1 g of a palladium/charcoal catalyst (1%) is added and hydrogenation is carried out at 70° C until the absorption of hydrogen has ceased. The catalyst is then filtered off, the solvent distilled off and the residue is fractionated through a descending condenser. 21 g of 2,6,10-trimethyl-dodecan-1-al are obtained (yield, 93% of theory). B.p. = 80° – 81° C at 0.3 mm Hg; $n_D^{25}$ = 1.4456. Odor: bitter, greener and more aldehyde-like orange scent.

I claim:
1. 2,6,10-trimethyl-dodeca-4,8-dien-1-al.
2. 2,6,10-trimethyl-dodecan-1-al.

* * * * *